United States Patent [19]

Cotter et al.

[11] Patent Number: 4,678,807
[45] Date of Patent: Jul. 7, 1987

[54] METHOD FOR DIRECTED VISCERAL METABOLISM OF MEDIUM CHAIN TRIGLYCERIDES

[75] Inventors: Richard Cotter, Libertyville; Robert C. Johnson, Westchester; W. Bruce Rowe, Chicago; Susan K. Young, North Chicago, all of Ill.

[73] Assignee: Baxter Travenol Laboratories, Inc., Deerfield, Ill.

[21] Appl. No.: 584,974

[22] Filed: Mar. 1, 1984

[51] Int. Cl.$^4$ .............................................. A61K 31/23
[52] U.S. Cl. ................................... 514/552; 514/838; 514/893; 514/943
[58] Field of Search ............... 424/312; 514/552, 838, 514/893, 943

[56] References Cited

U.S. PATENT DOCUMENTS 4,423,072 12/1983 Stahly ................................... 424/312
4,528,197 7/1985 Blackburn ........................... 514/552

FOREIGN PATENT DOCUMENTS 0071995 2/1983 European Pat. Off. ............ 514/552

OTHER PUBLICATIONS

Eckart et al., J. Parent. Int. Nat. 4(4):360–366, 1980.
Chem. Abst., 97:214639s, 1982.
Chem. Abst., 95:113913e, 1981.

Primary Examiner—Johnnie R. Brown
Assistant Examiner—John W. Rollins
Attorney, Agent, or Firm—Susan B. Fentress; Paul C. Flattery

[57] ABSTRACT

Method for providing caloric nutrition via liquid emulsions, to a patient with dysfunctional visceral organ comprising parenterally administering to the patient a lipid emulsion containing from about 10% to 50% by weight of long chain triglycerides and the remaining lipid being medium chain triglycerides.

14 Claims, No Drawings

METHOD FOR DIRECTED VISCERAL METABOLISM OF MEDIUM CHAIN TRIGLYCERIDES

BACKGROUND

This invention relates to the parenteral nutrition of patients. It is particularly concerned with providing caloric nutrition via lipid emulsions.

Lipid emulsions for parenteral nutrition are available commercially or can be manufactured in accordance with known processes. Generally, such emulsions have been made using the triglycerides of long chain fatty acids (LCTs). LCTs are obtained conventionally from soybean or safflower oil. Long chain fatty acids are fatty acids having 14 or more carbon atoms, usually 16 or 18 carbon atoms.

More recently, lipid emulsions for intravenous nutrition which contain triglycerides of medium chain fatty acids (MCTs) have become available. MCTs are triglyceride esters of fatty acids which contain a preponderance of $C_8$ and $C_{10}$ fatty acids (caprylic and capric acid, respectively). Emulsions of this type are disclosed in European Patent Application 0071995 and Eckart et al., "Journal of Parenteral and Enteral Nutrition" v 4(4):360-366, 1980. The above cited European patent application discloses an isotonic emulsion of LCTs and MCTs for parenteral use which contains a fat content of 3 to 30%, an LCT/MCT ratio between 4/1 and 1/4, a physiologically unobjectionable polyhydric alcohol and egg phosphatide as emulsifier.

MCTs are believed to be primarily metabolized in the liver, at least when administered orally, but a substantial proportion of MCTs are metabolized in the peripheral organs such as muscle. Since MCTs are more readily used for caloric energy than LCTs it would be desirable to ensure that exogenously administered MCTs are metabolized by organs having high energy requirements consequent to tissue repair and regeneration. Also, it would be desirable to reduce metabolism of MCTs by healthy organs in order to lessen the release of medium chain fatty acids from the MCTs, thereby sparingly potential medium chain fatty acid toxicity.

Thus a need exists for reducing MCT metabolism in the organs of the body not involved directly in such tissue repair and regeneration.

SUMMARY

We have discovered that a proportion of LCTs in MCT emulsions will act to substantially reduce the peripheral metabolism of MCTs without affecting the MCT metabolism of visceral organs, thereby enabling MCTs to be reserved for the caloric nutrition of the visceral organs. This proportion is less than about 50% by weight LCTs in an LCT and MCT mixture (hereafter all percentages are by weight unless otherwise stated), preferably from about 10% to about 33% LCTs.

DETAILED DESCRIPTION

The viscera are defined as the liver, kidney, intestines and other anchnic organs. The peripheral tissue includes all other organs, particularly bones, muscle and skin.

Dysfunction of the visceral organs may occur through a variety of agents. Disease, trauma or other insults are typical. Examples include wounds, blunt trauma, organ transplantation and a variety of diseases such as non-diabetic kidney disease, Crohn's disease, septicemia, peritonitis and alcoholic cirrhosis. Frequently the treatment of dysfunctional organs will call for total parenteral nutrition since the patient in most cases will not be capable of digesting food taken enterally. For example, esophageal varicies contraindicate the use of oral feeding tubes in cirrhotic patients and the dysfunctional intestines of Crohn's disease or inflammatory bowel syndrome are incompatible with oral food intake.

The MCTs to be used herein will be the triglycerides of $C_6$, $C_8$, $C_{10}$ and/or $C_{12}$ fatty acids in which the proportions of these fatty acids range in weight percent about from 0% to 3%, 50% to 100%, 50%-100% 0% to 3%, respectively. Usually only the $C_8$ and $C_{10}$ fatty acids will be present in ratios of about from 1:3 to 3:1. Preferably, the proportions of $C_6$, $C_8$, $C_{10}$ and $C_{12}$ fatty acids will be <2%, 65-80%, 20-35% and <2%. The MCT compositions can contain free fatty acids at up to about 0.005/mEq/g (USP), will have a saponification value of about from 325-365 (USP) and an iodine value (USP Method II) of up to about 1.0 $gI_2$/100 g. Color (Lovibond, AOCS Cc 13 h.45) is preferably 1.0 R. Unsaponifiable matter (USP), hydroxyl value (USP), and heavy metals (USP Method II) should be less than about 1.0%, 10.0 and 10 ppm, respectively. The refractive index (USP) and specific gravity (USP) range from about 1.440 to 1.460 and 0.920 to 0.960, respectively. These specifications are not critical. MCT oils of this type are commercially available as lauric oils from coconut oil. The exact specifications, including the relative proportions of $C_6$ to $C_{12}$ medium chain fatty acids, will vary somewhat since the MCTs are obtained from natural sources.

LCT emulsions are available as the Intralipid or Travamulsion ™ products, or they may be made by known processes. The oil used in the emulsion is usually soybean oil.

The MCTs are present with the LCTs in the oil phase of an oil-in-aqueous emulsion. The proportion of MCTs to LCTs is no less than about 1:1 by weight. The sparring effect of LCTs on peripheral MCT metabolism is largely fully achieved at an MCT:LCT proportion of about 2:1. Higher proportions of LCTs than 1:1 will not provide any further benefit to the visceral organs, and in fact may be undesirable in generating fatty deposits in visceral organs.

The MCT-containing emulsions may contain other substances besides LCTs. These include surfactants such as egg or soya phospholipid, tonicity adjusting agents such as glycerol, carbohydrate nutrients such as dextrose, and electrolytes, amino acids, vitamins and trace minerals. The concentration by weight of the oil in the emulsion is about from 5% to 20% being preferred.

The exact proportions of MCTs to LCTs selected will depend upon the metabolic state of the individual patient. This will vary as a function of complications or other diseases or injury than those affecting the viscera. Further, the input of MCTs and LCTs by enteral nutrition, to the extent the patient's condition makes this possible, should also be taken into account. Accordingly, the MCT metabolism of each patient is desirably monitored in order to arrive at the optimal ratio of MCTs to LCTs in the parenterally administered fat emulsion. Monitoring is by way of direct or indirect measurement of acetyl CoA synthesis in the viscera as opposed to the periphery. MCT emulsions ordinarily are metabolized throughout the body. Beta oxidation of the medium chain fatty acids hydrolyzed from the MCTs produces acetyl CoA in all tissues. Acetyl CoA is metabolized by the Krebs cycle to yield energy and $CO_2$. Acetyl CoA is shuttled into the synthesis of ketone bodies (acetoacetic acid and beta hydroxybutyrate) by the viscera, particularly kidney and liver. On the other hand, excess acetyl CoA generated in the peripheral organs, particularly muscle, acts to inhibit pyruvate dehydrogenase. This leads to an accumulation of lactate which is evidenced by elevated lactate concentrations in the plasma. Since it is desired in MCT nutrition of patients with visceral organ dysfunction to minimize peripheral metabolism of the MCTs, one should use a proportion of LCTs that minimizes excess acetyl CoA in the periphery. Monitoring the site of MCT metabolism is most conveniently followed by measuring a lipid metabolite, preferably an indirect metabolic signal of acetyl CoA levels since it is impractical to measure tissue acetyl CoA in the ordinary clinical setting. Suitable testing conveniently is accomplished by use of two assays, lactic acid and/or ketone bodies (ordinarily acetoacetate or beta-hydroxybutyrate). These substances may be determined by widely-available, standard clinical laboratory procedures. Upon the initial determination of a serum value for each substance after infusion of a fat emulsion having a given MCT to LCT ratio, the LCT proportion is adjusted upward in order to reduce the serum lactic acid concentration and maintain the concentration of ketones at above normal levels. Ideally, the LCT proportion will be adjusted to yield a normal plasma lactic acid level, i.e. from about 8.1 to 15.2 mg/dl, preferably about 10 mg/dl, while the ketones beta-hydroxy butyrate and acetoacetate, respectively, should range about from 1.5 to 25 times normal plasma levels, e.g. 600 to 850 μmoles/l and about 400-600 μmoles/l preferably about 700 μmoles/l and 500 moles/l. Plasma samples should be drawn from patients at about the same times (ordinarily about 6 hours) following infusion of the test emulsions in order to ensure that the results are comparable.

The lipid particles in the emulsion will have a diameter of less than about 0.75 μm and preferably less than about 0.5 μm. The emulsions will be sterile and ordinarily are packaged in glass or plastic containers. They can be made by known methods. For example, see U.S. Pat. No. 3,169,094 and European Patent Application 0071995.

The contribution of lipid to total nonprotein calories in the emulsions herein ordinarily will range from 20% to 80%. Thus, the MCTs in the emulsion will make up about from 5% to 60% of the total nonprotein calories in the emulsions, preferably about from 15% to 60%. For example, in a 70 Kg man receiving 40 kcals/Kg BW/day, MCT dosage may vary about from 0.35 mg/Kg BW/min to 2.05 mg/Kg BW/min, preferably about from 0.5 mg/Kg BW/min to 1.00 mg/Kg BW/min and optimally about from 0.5 to 0.75 mg/Kg BW/min. The remaining nonprotein calories are supplied by LCTs and, preferably carbohydrates.

A convenient method for preparing and administering the emulsion herein is for the hospital or user pharmacy to sterile mix the emulsion components using commercially available equipment. The MCT and LCT emulsions are mixed with sterile aqueous solutions of other desirable additives: amino acids in proportions suitable for parenteral nutrition, vitamins, carbohydrates such as dextrose, electrolytes such as potassium and sodium chloride, drugs, and trace minerals such as zinc ions. The resulting product is a sterile emulsion of MCTs and LCTs in an aqueous solution in proportions characterized above, containing amino acids carbohydrate, and, optionally, drugs, trace minerals and vitamins. Alternatively, and less preferably, the MCTs and LCTs can be mixed as oils, then emulsified and combined with the other additives noted above. Drugs which have heretofore been conventionally administered to patients with dysfunctional visceral organs, e.g., antibiotics and steroids may be included in the emulsion.

The emulsions herein are packaged and stored in hermetically sealed containers for long and short-term storage. The additives to be included in the emulsions will depend upon how long the emulsions are to be stored. Long-term storage is acceptable for emulsions with aqueous phases containing sugar, the amino acids, and some electrolytes. Dextrose should not be included in emulsions prepared for long-term storage.

The following examples are intended to be illustrative and should not be construed to limit the claims.

EXAMPLE 1

In a suitable mixing vessel are mixed 2.0 kg of MCT oil consisting of approximately 75% octanoic acid and 25% decanoic acid by weight, 120 g of purified egg phospholipids, 225 g of glycerol, USP, and a suitable quantity of water for injection, USP. The mixture is agitated in order to produce a coarse emulsion. This emulsion is then homogenized repeatedly at high pressure to produce an emulsion of mean particle diameter of less than 0.75 μm. During the process, the pH of the emulsion is adjusted to a physiological range with sodium hydroxide. The final volume is adjusted, if necessary, with water for injection, USP, to 10 liters and the emulsion filtered into glass containers and heat-sterilized. A mixed LCT-MCT emulsion was prepared by combining 1508 mls of the 20% MCT emulsion with 742 mls of a 20% soybean oil emulsion (Travamulsion TM 20%; Travenol Laboratories, Inc.) in a 3-liter plastic bag suitable for intravenous admixtures (Travamulsion TM container).

EXAMPLE 2

Example 1 was repeated except that the MCT emulsion contained radioactive trioctanoin (glycerol tri[1-$^{14}C$]octanoate) and the ratio of MCT to LCT in the mixed emulsion was 75:25. The LCT in the mixed emulsion was not radioactive. The control was a 20% soybean oil emulsion containing radioactive trilinolein (glycerol tri[1-$^{14}C$]linoleate) prepared in accordance with procedures generally known to those skilled in the art.

Male 175–300 g Sprague-Dawley rats were randomly assigned to three treatment groups (MCT alone, 75% MCT:25% LCT, or LCT alone). Each animal was fasted for 12 hours and then was injected in a tail vein with approximately 1 μCi of $^{14}C$ in a bolus dose of 0.402 g lipid/Kg body weight. At the termination times after injection the animals were stunned and then killed by cervical dislocation. Liver tissue samples then were removed for radioactive counting. Samples were taken at the times noted in Table 1 below. Each data point represents a single animal.

TABLE 1

| Termination | Liver radioactivity (dpm/100 mg) | | |
|---|---|---|---|
| Time | MCT alone | 75:25 MCT:LCT | LCT alone |
| 30 min. | 3400 | 5000 | 300 |
| 2 hours | 880 | 630 | 5200 |
| 4 hours | 500 | 173 | 1950 |
| 8 hours | 500 | 200 | 1750 |

The data in table 1 show that the presence of LCT in the MCT emulsion results in considerably greater levels of MCT metabolism in the liver than when compared to MCT alone, even though the administered radioactivity in the LCT-MCT mixed emulsions was one fourth less than in the MCT emulsion because of dilution by the unradioactive LCT emulsion. Without wishing to be bound by any theoretical hypothesis to explain this phenomenon, it is believed that common metabolic pathways exist in the peripheral organs for LCT and MCT metabolism, and that LCTs displace MCTs in such pathways. This is not the case with visceral organs like the liver, where an increased ratio of LCTs does not inhibit MCT metabolism. The results with the LCT group indicate that LCT has a low affinity for liver MCT binding sites. The elevated liver radioactive levels which occur at 2 hours and later are attributed to free fatty acids released from LCT by other organs and transported to the liver for packaging into very low density lipoprotein, deposited as fatty deposits and, to a minor degree used for energy. The net result is over 50% more energy substrate made available to the liver by incorporation of LCT into the MCT emulsion. This is expected to promote tissue repair and regeneration. Similar results could be expected for the intestines and kidney.

EXAMPLE 3

The experiment of Example 2 was repeated except that the ratio of MCT to LCT was 67% MCT to 33% LCT, the dosage was 1.6 g of MCT/Kg of rat body weight or 2.4 g of mixed emulsion/Kg. As in the previous study, the LCT in the mixed emulsion was not radioactive. The sampling point was at two hours.

In addition, blood samples were taken from each rat by cardic puncture immediately prior to sacrifice and the plasma obtained. The results are shown in Table 2.

TABLE 2

| Emulsion | Sample | MCT Radioactivity found in Sample as % of dose |
|---|---|---|
| MCT alone | Plasma | 0.83 |
|  | Liver | 2.8 |
| Mixed Emulsion | Plasma | 3.4 |
|  | Liver | 4.6 |

This example confirms the increased level of MCT incorporated into the liver in the presence of LCT. The circulating MCT level also is higher in the case of the mixed emulsion. This is hypothesized to be a function of MCT displacement by LCT from peripheral receptors by LCT, or prevention of MCT binding by LCTs, thereby making MCTs available to visceral organs for longer periods and at higher concentrations in the absence of LCTs.

EXAMPLE 4

This contemplated example describes the clinical use of the mixed emulsions for the nutrition of a visceral trauma patient. The patient is a 22-year old male auto accident victim. In the emergency room, the patient presented with frank shock (bp 60/40) with severe pulmonary failure in association with intraabdominal bleeding and multiple pelvic fractures. After initial resuscitation, he was taken to the operating room where an exploratory laporatomy was performed. This procedure revealed bleeding from lacerations of the liver and perforations of the small bowel. These lacerations and perforations were repaired and the patient placed in the ICU ward. From days 1 through 10 the patient's metabolic profile indicated a steadily declining plasma albumin (3-4 mg% to 2.7 mg%). Plasma bilirubin increased from .7 to 25 ml/100 ml. Liver enzymes showed elevated values in the ranges of alkaline phosphatase 30 u/l (normal is less than 17 u/l) SGOT 1000 u/l (normal is less than 50 u/l), SGPT 800 u/l (normal is less than 40 u/l), and LDH 240 u/ml (normal is less than 98 u/l). Prothrombin times were somewhat decreased. The patient was continuously hyperglycemic. The leukocyte count began to rise and blood cultures were positive as the patient's temperature rose to 103° to 104° F., indicating sepsis. The patient's level of consciousness varied from lethargic to comatose.

Nutritional support was indicated because of the patient's reduced visceral protein status and other indices of deteriorating nutritional status. Oral or tube feeding was not indicated due to the perforated small intestine. Total parenteral nutrition was the only way nutrients could be administered safely and effectively. A central vein catheter was inserted into the patient's superior vena cava. Nutritional support for the patient was set at a calorie requirement of 70 kcal/Kg BW/day and protein (amino acid equivalents) at 1.5 g/Kg BW/day. The amino acid source was a standard amino acid mixture (Travasol ® amino acids). The remaining 64 kcal/Kg BW/day were administered at 65% glucose and 35% as a physical admixture of 20% MCT emulsion and 20% LCT emulsion. The proportions of MCT and LCT were adjusted over the range of 30 to 50% by weight of LCTs in order to optimize plasma ketone and lactic acid levels noted above based on frequent assays. If lactate levels were higher than normal, the proportion of LCT was increased, but not so as to reduce the ketones to lower than the bottom of the range noted above. This regimen leads to a daily glucose intake of 7.2 mg/kg/min, LCT intake of approximately 0.57 to 0.86 mg/kg/min, and MCT intake of approximately 0.97 to 1.3 mg/kg/min. Electrolytes, vitamins, and trace elements were administered to meet the established requirements of the patient.

The patient's condition improved in the course of the next ten days on this therapy. Clinical parameters indicated liver repiar, visceral protein recovery, and small intestine recovery as a result of this specific therapy directed at the liver and small bowel.

What is claimed is:

1. A method of providing caloric nutrition to a dysfunctional visceral organ comprising parenterally administering to a patient with a dysfunctional visceral organ an effective amount of a lipic emulsion containing about from 10% to 50% by weight of LCT and the remaining lipid being MCT to thereby shift the supply of MCT energy substrates to the visceral organs and limit the availibility of MCT to the peripheral organs.

2. The method of claim 1 wherein the organ is a transplant.

3. The method of claim 1 wherein the organ is the intestines.

4. The method of claim 3 wherein the intestines are dysfunctional because of injury or inflammatory bowel disease.

5. The method of claim 1 wherein the organ is other than the liver.

6. The method of claim 1 wherein the organ is diseased.

7. In a method wherein a lipid emulsion containing MCT and LCT is parenterally administered to a patient to provide caloric nutrition to a dysfunctional visceral organ, the improvement comprising monitoring the concentration of at least one lipid metabolite in the body fluid of the patient and, in response to such concentration, adjusting the relative proportions of MCT to LCT in the lipid emulsion to thereby direct the MCT metabolism to or from the peripheral and visceral organ as required.

8. The method of claim 7 wherein the metabolite is a ketone or lactic acid.

9. The method of claim 8 wherein the ratio is adjusted in order to maintain the lactic acid concentration at normal levels and the ketone concentration at about from 1.5 to 2.5 times normal levels.

10. The method of claim 9 wherein the lactic acid concentration is adjusted to range from 8.1 to 15.2 mg/dl.

11. The method of claim 9 wherein the beta-hydroxybutyrate or acetoacetate levels are adjusted to range from 600 to 850 u moles/l or 400 to 600 u moles/l, respectively.

12. The method of claim 7 wherein the metabolite is acetoacetate or beta-hydroxybutyrate.

13. The method of claim 7 wherein the metabolite is acetyl CoA, its metabolic products or products of enzymes allosterically inhibited thereby.

14. The method of claim 7 wherein the lipid metabolite is a ketone body.

* * * * *